United States Patent [19]

Chiesi et al.

[11] Patent Number: 4,690,944

[45] Date of Patent: Sep. 1, 1987

[54] HOMOCYSTEINE THIOLACTONE DERIVATIVES, PROCESS FOR THE PREPARATION THEREOF AND PHARMACEUTICAL COMPOSITIONS THEREFROM

[75] Inventors: Paolo Chiesi; Vittorino Servadio, both of Parma, Italy

[73] Assignee: Chiesi Farmaceutici S.p.A., Parma, Italy

[21] Appl. No.: 831,159

[22] Filed: Feb. 19, 1986

[30] Foreign Application Priority Data

Feb. 22, 1985 [IT] Italy .................. 19621 A/85

[51] Int. Cl.$^4$ .................. A61K 31/38; C07D 409/00; C07D 333/36
[52] U.S. Cl. .................. 514/445; 514/336; 514/444; 546/284; 549/60; 549/63
[58] Field of Search .................. 549/63, 60; 546/284; 514/444, 445, 336

[56] References Cited

U.S. PATENT DOCUMENTS 4,411,909 10/1983 Gonella .................. 549/63

Primary Examiner—Alan Siegel
Attorney, Agent, or Firm—Bucknam and Archer

[57] ABSTRACT

Compounds of formula I

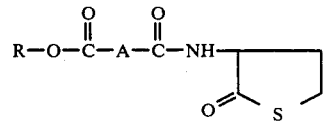

wherein A represents:
a saturated cyclic or heterocyclic aromatic or heteroaromatic residue;
a saturated or unsaturated bicyclic residue; and R represents H, an alkyl, cycloalkyl or alkoxyalkyl group.

Compounds I are endowed with valuable therapeutic characteristics.

6 Claims, No Drawings

HOMOCYSTEINE THIOLACTONE DERIVATIVES, PROCESS FOR THE PREPARATION THEREOF AND PHARMACEUTICAL COMPOSITIONS THEREFROM

The present invention relates to novel 3-aminodihydro-2(3H)-thiophene (ADT) or homocysteine thiolactone derivatives, a process for the preparation thereof and pharmaceutical compositions containing them.

More particularly, the invention relates to compounds of generale formula I

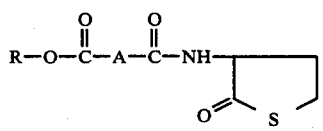

wherein A represents:
a saturated mono or bicyclic residue; a $C_3$-$C_6$ monocyclic unsaturated residue; an aromatic or heteroaromatic residue, which may be optionally substituted on their turn by alkyl, amino or alkoxy groups;
a saturated or unsaturated bicyclic residue having $C_3$-$C_4$ to $C_6$-$C_6$ ring systems, preferably bicyclo-[2,2,1]-epta-5-ene-1,2-diyl or bicyclo-[2,2,2]-octa-5-ene-1,2-diyl, optionally containing one or more heteroatoms, such as S or O, and alkyl substituent groups;
R represents H, a $C_1$-$C_4$ straight or branched alkyl group, an alkoxyalkyl group or a $C_5$-$C_8$ saturated or unsaturated cyclic residue, optionally substituted.

Particularly preferred compounds are those in which A represents 1-2, 1-3 or 1-4 cyclohexyl groups; 1-2 or 1-3 cyclopentyl groups; 1,2-decahydronaphthalenyl group; 4-cyclohexene-1,2-yl or 1-cyclohexane-1,2-yl groups; 1-2, 1-3 or 1-4 phenylene groups; 2-3, 2-4 or 2-5 pyridyl groups.

When R is H, compounds I may be salified with pharmaceutically acceptable organic or inorganic bases, said salts being another object of the present invention. Compounds of formula (I) may be in racemic, diastereoisomeric or optically active form, all these forms falling within the scope of the present invention.

The novel homocysteine thiolactone derivatives object of the present invention show such valuable pharmacological characteristics, as to be used in therapy as mucosecretolytic, antiinflammatory or hepatoprotecting agents.

The process for the preparation of homocysteine thiolactone derivatives of general formula (I) consists in reacting homocysteine thiolactone with a dicarboxylic derivative, such as a mono- or dihalide or mono- or diester, or preferably with a cyclic anhydride of a dibasic acid, in an appropriate solvent.

Homocysteine thiolactone may be used in form of base or hydrochloride: in the latter instance, the reaction mixture must be added with an equivalent amount of an organic base, such as triethylamine, or an inorganic base, such as alkali or alkali-earth metal hydroxides, bicarbonates or carbonates.

Preferred solvents are apolar aprotic solvents, such as benzene, cyclohexane, etc., or polar aprotic solvents, such as methylene chloride, chloroform, ethyl ether, dimethylformamide, or polar protic solvents, such as water or ethanol.

The reaction may be carried out at temperatures ranging from 0° C. to the solvent's reflux temperature, for a time from 1 to 10 hours, depending on the nature of the reagents and solvents.

The salts object of the invention may be obtained by addition of equivalent amounts of inorganic bases, such as alkali or alkali-earth metal hydroxides or carbonates, or organic bases, preferably aminoacids, such as lysine or arginine, in a polar medium.

The invention will be illustrated in further detail by means of the following non-limiting examples.

EXAMPLE 1

2-[[N-(tetrahydro-2-oxo-3-thienyl)amino]carbonyl]benzoic acid (II)

10 Grams (65 mmol) of DL-homocysteine thiolactone hydrochloride, 9.36 g (63.2 mmol) of phthalic anhydride and 5.46 g (65 mmol) of $NaHCO_3$ were added in a 250 ml reaction flask, containing 42 ml of $CH_2Cl_2$ and 1 ml of $H_2O$. The reaction mixture was stirred for about 10 hours, then filtered.

The resulting solid residue was added with 200 cc of water, heated to 50° C. and stirred for a while. The mixture was left to stand at room temperature, filtered and dried in oven under vacuum.

14.51 Grams of the compound were obtained (86.5% yield), m.p. 152°–156° C.

M.F.=$C_{12}H_{11}NO_4S$
MW=265.31

Elemental analysis calc. % C: 54.34; H: 4.18; N: 5.28. found % C: 54.25; H: 4.04; N: 5.28.

The IR and NMR spectra were consistent with the above formula.

According to the same procedure, 10 g (65 mmol) of DL-homocysteine thiolactone hydrochloride, 11.52 g (63 mmol) of DL-camphoric anhydride and 5.46 g (65 mmol) of $NaHCO_3$ in 42 ml of $CH_2Cl_2$ and 1 ml of $H_2O$ were reacted.

A white solid was obtained, melting at 188°–193° C. (III).

M.F.=$C_{14}H_{21}NO_4S$
MW=299.38

Elemental analysis calc. % C: 56.16; H: 7.07; N: 4.67. found % C: 53.85; H: 6.95; N: 5.46.

The IR and NMR spectra were consistent with the above formula.

The solid consisted of the following structural isomers:
3-[[N-(tetrahydro-2-oxo-3-thienyl)amino]carbonyl]-2,2,3-trimethyl-cyclopentanecarboxylic acid (IIIa)
3-[[N-(tetrahydro-2-oxo-3-thienyl)amino]carbonyl]-1,2,2-trimethyl-cyclopentanecarboxylic acid (IIIb)
which were separated by conventional techniques, particularly chromatography.

EXAMPLE 2

A solution of 11.2 g (0.1 mol) of DL-homocysteine thiolactone and 13.8 ml (0.1 mol) of triethylamine in 100 ml of anhydrous ethyl ether was slowly added to a solution containing 28.8 ml (0.2 mol) of phthaloyl dichloride in 300 ml of anhydrous ethyl ether.

The mixture was stirred at room temperature for 2 hours, the obtained solution was filtered and dried. The residue was taken up in 600 ml of chloroform and 300 ml of a 5% NaHCO$_3$ solution were added under stirring.

At the end of the reaction (end of CO$_2$ evolution), the layers were separated, the CHCl$_3$ layer was washed with H$_2$O, dried over Na$_2$SO$_4$ and dried under vacuum.

The residue was treated with water, filtered, washed with H$_2$O and dried under vacuum, to obtain 18.5 g (71% yield) of a crystalline white solid (compound II).

EXAMPLE 3

3-[[N-(Tetrahydro-2-oxo-3-thienyl)amino]-carbonyl]-bicyclo[2,2,1]-ept-5-ene-2-carboxylic acid (IV)

8.29 Grams (50.5 mmol) of nadic anhydride (cis-endo-5-norbornene-2,3-dicarboxyl anhydride) were added to a solution of 6.09 g (52 mmol) of homocysteine thiolactone in 800 ml of CH$_2$Cl$_2$.

The mixture was stirred at room temperature for 10 hours, then dried and 100 ml of ethyl ether were added to the resulting solid.

After keeping at 0° C. for 4 hours, the solid was filtered and dried in oven under vacuum, at 40° C.

13.36 g (91.4% yield) of a white solid were obtained, m.p. 175°–181° C.

M.F.=C$_{13}$H$_{15}$NO$_4$S
MW=281.32

Elemental analysis calc. % C: 55.51; H: 5.38; N: 4.98. found % C: 55.46; H: 5.32; N: 5.01.

The IR and NMR spectra were consistent with the above formula.

According to the same procedure, 15.25 g (0.13 mol) of homocysteine thiolactone were reacted with 21.38 g (0.122 mol) of 4-methyl-1,2-cyclohexyl-dicarboxylic anhydride in 180 ml of CH$_2$Cl$_2$. A white solid was obtained, melting at 153°–160° C.

M.F.=C$_{13}$H$_{19}$NO$_4$S
MW=285.36 (V)

Elemental analysis calc. % C: 54.71; H: 6.71; N: 4.90. found % C: 55.00; H: 6.86; N: 4.88.

The IR and NMR spectra were consistent with the above formula.

The solid consisted of the following structural isomers:

2-[(N-tetrahydro-2-oxo-3-thienyl)amino)carbonyl]-4-methyl-cyclohexanecarboxylic acid (Va)

2-[(N-tetrahydro-2-oxo-3-thienyl)amino)carbonyl]-5-methyl-cyclohexanecarboxylic acid (Vb)

which were separated by conventional techniques, particularly chromatography.

The following compounds may be prepared analogously:

2-[(N-tetrahydro-2-oxo-3-thienyl)amino)carbonyl]-4-cyclohexenecarboxylic (VI); m.p. 133°–138° C.; the IR and NMR spectra were consistent with the above formula;

2-[(N-tetrahydro-2-oxo-3-thienyl)amino)carbonyl]-cyclohexanecarboxylic acid (VII); m.p. 147°–150° C.; the IR and NMR spectra were consistent with the above formula;

2-[(N-tetrahydro-2-oxo-3-thienyl)amino)carbonyl]-3-pyridinecarboxylic acid (VIII); m.p. 143°–146° C.; the IR and NMR spectra were consistent with the above formula;

3-[(N-tetrahydro-2-oxo-3-thienyl)amino)carbonyl]-bicyclo[2,2,2]-oct-5-ene-2-carboxylic acid (IX); m.p. 153°–158° C.; the IR and NMR spectra were consistent with the above formula.

By condensing the above described acids II–XI with primary, secondary, and tertiary alcohols, the corresponding esters were obtained.

Compounds of general formula (I) according to the present invention, show valuable pharmacological characteristics, particularly antiinflammatory and mucosecretolytic activities, therefore, compounds (I) may be advantageously used in humans, for the treatment of respiratory apparatus diseases, such as bronchitis, tracheobronchitis, pharyngitis, rhinopharyngitis, etc.

The pharmacological tests have been carried out using as reference compounds similar well-known substances, commonly used in therapy for the treatment of the above pathological conditions.

TOXICITY AFTER SINGLE ADMINISTRATION

IVA:NMRI (SPF) mice, fasted for 18 hours before treatment with water ad libitum, have been used. The compounds, dissolved or suspended in a 0.2% Tween ® 80 aqueous solution, have been administered orally, at constant concentration (10%). According to the death-rate observed after 7 days from treatment, the approximate LD$_{50}$ values, reported in Table 1, have been interpolated on Probits chart.

MUCOSECRETODYNAMIC ACTIVITY

Male IVA-NMRI (SPF) mice, housed for at least 1 week in standard conditions, fasted (water ad libitum) for 18 hours before treatment, have been used.

The used method, relying on the fluorescein ability to be excreted even in the respiratory tract, is according to Mawatari H. (Kagoshima Daigaku Igaku Zasshi 27, 561, 1976) and to Graziani G. and Cazzulani P. (Farmaco (Pra) 36, 167, 1981).

The compounds, dissolved or suspended in 20 ml/kg of a 0.2% Tween ® 80 aqueous suspension, were administered orally 90 minutes before the intravenous injection of 1% (5 ml/kg) fluorescein. Animals treated p.o. with the only vehicle were used as a control group. After 30 minutes from the fluorescein injection the animals were killed and subjected to incannulation of the trachea. Then the respiratory tract was washed and the spectrophotometric dosage of the fluorescein was carried out against phosphate buffer on the so collected eluate, suitably diluted with phosphate buffer and centrifugated.

The amount of fluorescein was determined by means of a calibration curve prepared in the same experimental conditions and the excretion expressed as ng/hour/10 g body weight. For each experimental session the percent increases of excretion versus controls were calculated. According to said values the regression log dose-effect straight-lines were determined and the ED$_{50}$ values, reported in Table 1, were interpolated.

"IN VITRO" MUCOLYTIC ACTIVITY 0.2 Ml of a 10% DMSO solution of the compounds under exam have been homogeneously added to 1.8 ml of a 6% aqueous solution of porcine gastric mucine (Kock-Light 4065-00, batch 81063). Control samples were similarly added with the vehicle only. After incubation at 25° C. for 30 minutes, the analysis of the rheologic characteristics was carried out by means of Contraves Low-Shear 30 sinus viscosimeter endowed with oscillating device for the study of the viscoelasticity. The dynamic measurements of the viscoelasticity were carried out at a single frequency (0.075 Hz), using an appropriate concentrical cylinder measurement system, particularly suited for bronchial mucus (Contraves MS-LS 1-1).

The rheogramm was recorded on X/Y Rikadenki 11T recorder and the viscosity (G') and elastic modulus ($\eta$) determination was carried out by means of vectorial calculation.

The percent decreases versus control samples, reported in Table 1, were determined from the means of the values of said parameters (at least 7 replications per sample).

TABLE 1

| Compounds | Acute toxicity $LD_{50}$ approx. mg/kg p.o. | "in vivo" flourescein test $ED_{50}$ mg/kg p.o. | Mucosecretodynamic-mucolytic activity "in vitro" % decrease | |
|---|---|---|---|---|
| | | | elasticity (G') | viscosity ($\eta$) |
| II (CHF 1210) | >4000 | 340 | 23 | 45 |
| III(CHF 1243) | >4000 | 180 | 27 | 46 |
| IV (CHF 1203) | >4000 | 25 | 32 | 43 |
| V (CHF 1229) | >4000 | 80 | 28 | 49 |
| S—carboxymethyl-cysteine | >4000 | 1900 | N.D. | N.D. |
| N—acetyl-L-cysteine | 4400 | 1300 | 39 | 53 |

N.D. = Not determined.

The compounds under exam possess a remarkable mucosecretodynamic-mucolytic activity, particularly in the fluorescein "in vivo" test, wherein similar reference compounds exhibit a relatively modest activity.

The present invention refers moreover to pharmaceutical compositions containing as an active principle a compound of formula (I), as defined above, as such or in form of a pharmaceutically acceptable salt thereof, in combination with at least one pharmaceutically acceptable excipient.

The compositions may be administered by the oral, rectal, parenteral route or by inhalation, respectively, in form of capsules, tablets, granules, suspensions, syrups or the like, suppositories, solutions, suspensions or powders respectively for the parenteral or inhalatory route.

For the preparation of pharmaceutical compositions for the oral administration in unitary dose, the active principle may be mixed with a solid, powdered excipient such as lactose, saccharose, sorbitol, mannitol, potato, cereal or maize starch or amylopectine, a cellulose derivative or gelatine, and it can comprise also lubricants such as talc, magnesium or calcium stearate, polyethylenglycol or silica. The tablets can be variously coated according to well known methods in the pharmaceutical practice. Hard gelatine capsules may comprise granules of the active principle together with solid, powdered excipient such as lactose, saccharose, sorbitol, mannitol, starches of the above cited kind, cellulose derivatives or gelatine, and they may comprise also stearic acid or magnesium stearate or talc.

Granules in sachets may be prepared from cellulose derivatives, precipitated silica, flavours and sugars or polyalcohols such as saccharose, mannitol, sorbitol etc.

For the preparation of suspensions for oral use, the active principles may be dissolved in aqueous solutions of sugars or polyalcohols with the addition of preservatives and flavouring agents.

Unitary doses for the rectal administration may be in form of suppositories containing the active principle in combination with a neutral fatty base (i.e. fatty acid glycerides) or with hydrosoluble or self-emulsifying excipients (i.e. polyethylenglycol mixtures).

For injectable formulations for parenteral administrations, the excipients may be a sterile, pharmaceutically acceptable liquid such as water or a polyvinylpyrrolidone aqueous solution or again an oil such as peanut oil and optionally a stabilizing and/or buffering agent.

The unitary dose for the formulations for oral use such as tablets, capsules, granules and for rectal, parenteral or inhalatory formulations may range from 10 to 500 mg of active principle. The concentration of the active principle in the suspensions for oral use may range from 0.1 to 5%.

The following formulations are reported by way of example.

| Formulation in capsules - Composition with two different dosages | | | |
|---|---|---|---|
| Compound of Example 3 | mg | 100 | 200 |
| Starch | mg | 20 | 30 |
| Lactose | mg | 172 | 57 |
| Polyvinylpyrrolidone | mg | 5 | 10 |
| Magnesium stearate | mg | 3 | 3 |
| Formulation in sachets - Composition with two different dosages | | | |
| Compound of Example 3 | mg | 100 | 200 |
| Hydroxypropylmethylcellulose | mg | 25 | 50 |
| Precipitated silica | mg | 2 | 4 |
| Citrus fruit flavour | | q.s. | q.s. |
| Sorbitol q.s. to | g | 5 | 5 |
| Suspension for oral use | | | |
| Compound of Example 3 | mg | 1000 | |
| Carboxymethylcellulose | mg | 80 | |
| Microcrystalline cellulose | mg | 920 | |
| Sorbitol | g | 10 | |
| Methyl p-hydroxybenzoate | mg | 135 | |
| Propyl p-hydroxybenzoate | mg | 15 | |
| Citrus fruit flavour | | q.s. | |
| Purified water q.s. to | ml | 100 | |
| Formulation in suppositories - Composition with two different dosages | | | |
| (a) Compound of Example 3 | mg | 100 | 200 |
| Solid semi-synthetic glycerides q.s.to | mg | 2000 | 2000 |
| (b) Compound of Example 3 | mg | 100 | 200 |
| Butylhydroxyanisole | mg | 2 | 2 |
| Polyoxyethylenglycols q.s.to | mg | 2000 | 2000 |

We claim:

1. A compound of formula I

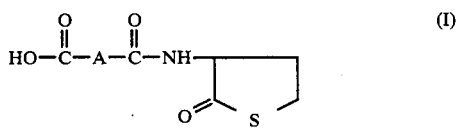

wherein —COACO— is the radical from 1,2-, 1,3-, 1,4-cyclohexane dicarboxylic acid, 1,2-, 1,3-cyclopentane dicarboxylic acid or A is 4-cyclohexene-1,2-yl or 1-cyclohexene-1,2-yl; 1-2, 1-3 or 1-4 phenylene; 2-3, 2-4 or 2-5 pyridyl, -bicyclo-[2,2,1]-hepta-5-ene-1,2-diyl; -bicyclo-[2,2,2]-octa-5-ene-1,2-diyl; -7-oxabicyclo-[2,2,1]-hepta-5-ene-1,2-diyl.

2. A compound which is a member selected from the group consisting of (1) 2-[[N-(tetrahydro-2-oxo-3-thienyl)amino]carbonyl]-benzoic acid;

(2) 3-[[N-(tetrahydro-2-oxo-3-thienyl)amino]carbonyl]-2,2,3-trimethyl-cyclopentanecarboxylic acid;

(3) 3-[[N-(tetrahydro-2-oxo-3-thienyl)amino]carbonyl]-1,2,2-trimethyl-cyclopentanecarboxylic acid;

(4) 3-[[N-(Tetrahydro-2-oxo-3-thienyl)amino]carbonyl]bicyclo[2,2,1]-ept-5-ene-2-carboxylic acid;

(5) 2-[(N-tetrahydro-2-oxo-3-thienyl)amino)carbonyl]4-methylcyclohexanecarboxylic acid;

(6) 2-[(N-tetrahydro-2-oxo-3-thienyl)amino)carbonyl]4-methylcyclohexanecarboxylic acid.

3. A compound according to claim 1 wherein A is unsubstituted phenylene or phenylene substituted by alkyl, amino or alkoxy, 5 or 6 membered cycloaliphatic which is unsubstituted or substituted by alkyl or bicyclo[2,2,1]hept-5-ene ring.

4. Pharmaceutical compositions having mucosecretolytic, antiinflammatory and hepatoprotecting activity containing as the active principle a compound according to claim 1 or a pharmaceutically acceptable salts thereof.

5. A pharmaceutical composition according to claim 4 in form of capsules, tablets, granules, suppositories or vials, containing from 10 to 500 mg of active principle per unit dose.

6. A pharmaceutical composition according to claim 4 in form of oral suspension containing the active principle in concentrations from 0.1 to 5%.

\* \* \* \* \*